United States Patent
Gourley et al.

(10) Patent No.: US 6,627,213 B2
(45) Date of Patent: Sep. 30, 2003

(54) INHIBITION OF NEONATAL HYPERBILIRUBINEMIA IN BREAST FED INFANTS

(75) Inventors: Glenn R. Gourley, Madison, WI (US); Bill L. Kreamer, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1 day.

(21) Appl. No.: 09/967,670

(22) Filed: Sep. 28, 2001

(65) Prior Publication Data

US 2002/0013267 A1 Jan. 31, 2002

Related U.S. Application Data

(63) Continuation-in-part of application No. 09/641,597, filed on Aug. 18, 2000.
(60) Provisional application No. 60/150,158, filed on Aug. 20, 1999.

(51) Int. Cl.[7] .......................... A61K 47/00; A61K 9/08; A61K 9/14
(52) U.S. Cl. .................. 424/439; 424/400; 424/489; 426/72; 426/74; 426/656; 426/801
(58) Field of Search ............................... 424/400, 439, 424/489; 426/72, 74, 801, 656

(56) References Cited

U.S. PATENT DOCUMENTS

| | | | |
|---|---|---|---|
| 4,753,926 A | 6/1988 | Lucas et al. | |
| 5,068,184 A | 11/1991 | Knuth et al. | |
| 5,212,235 A | 5/1993 | Nestaas et al. | |

FOREIGN PATENT DOCUMENTS

| | | |
|---|---|---|
| EP | 059775 A2 | 9/1982 |
| WO | WO 94/14458 A1 | 7/1994 |
| WO | WO 01/13743 A1 | 3/2001 |

OTHER PUBLICATIONS

Pp. 6, 7, 9, 10, 896, 897, 1008 and 1009 of the 1989 publication Deutsche Forschunganstalt Fur Lebensmittelschemie (ED.): Food Compositions and Nutrition Tables, Wissenschaftliche Verlagsgesellschaft MBH Stuttgart XP000213764 (in English).

G. Eisenbrand et al. (ED.): "Rompp Lexikon Lembensmittelchemie" 1995, Georg Thieme Verlag, Stuttgart, New York XP002153765 p. 10 and translation.

I. Matsuda et al., "Effects Of Aspartic Acid And Orotic Acid Upon Serum Bilirubin Level In Newborn Infants", 90 Tohoku J. Exp. Med. 133–136 (1966) and e–mail communication of May 11, 2000 with author.

A. Saito et al., "The Effect Of Aspartic Acid On . . . Bilirubin", 27 Shohni–ka–Shinryo 124–128 (1964) and partial crude translation.

D. Gray et al., "Effects Of Aspartic Acid, Orotic Acid, And Glucose On Serum Bilirubin Concentrations In Infants Born Before Term", 46 Arch. Dis. Child. 123–124 (1971).

G. Gourley, et al., "The Effect Of Diet Of Feces And Jaundice During The First 3 Weeks Of Life", 103 Gastroenterology 660–667 (1992).

G. Gourley, et al., "Inhibition Of Beta–Glucuronidase By Casein Hydrolysate Formula", 25 J. Ped. Gast. & Nutr. 267–272 (1997).

G. Gourley, "Bilirubin Metabolism And Kernicterus", 44 Advances in Pediatrics 173–229, Chapter 6 (1997).

G. Gourley et al., "Neonatal Jaundice And Diet", 153 Arch Pediatr Adolesc. 184–188 (1999).

(List continued on next page.)

Primary Examiner—James M. Spear
Assistant Examiner—Charesse Evans
(74) Attorney, Agent, or Firm—Quarles & Brady LLP

(57) ABSTRACT

Disclosed herein are infant supplements containing casein, a salt of casein, whey and/or a casein hydrolysate which are free of carbohydrate, and methods for their use with breast feeding babies. The supplements are designed to suppress serum bilirubin levels and the incidence and severity of neonate jaundice. In one form, a dose of such a supplement is mixed with human breast milk and fed to the neonate.

14 Claims, 2 Drawing Sheets

OTHER PUBLICATIONS

S. Vaisman et al. Pharmacologic Treatment Of Neonatal Hyperbilirubinemia, Clinics In Perinatology, Symposium On Drug Therapy In the Neonate, vol. 2, No. 1, 37–57 (1975).

V. Hurgoiu et al., Aspartofortul In Tratamentul Icterului La Prematuri, 34 Pediatria 189–192 (1985) and partial crude translation thereof.

A Jan. 13, 2000 consent form used in Applicants' clinical trials as reported in the application. Not believed to be prior art. This is representative of the form prospective and actual test subjects received and retained relating to the trial more than one year prior to the filing date of this application.

G. Gourley et. al., The Effect Of Saccharolactone on Rat Intestinal Absorption Of Bilirubin In the Presence Of Human Breast–Milk, 25 Ped. Res. 234–238 (1989).

B. Kreamer et al., A Novel Inhibitor Of Beta–Glucuronidase: L–Aspartic Acid, _____ Ped. Res. _____ (Oct. 2001) (not believed to be prior art—in press).

INHIBITION OF NEONATAL HYPERBILIRUBINEMIA IN BREAST FED INFANTS

CROSS-REFERENCE TO RELATED APPLICATIONS

This application is a continuation-in-part of U.S. Ser. No. 09/641,597 filed Aug. 18, 2000, which in turn claims priority based on U.S. provisional application 60/150,158 filed Aug. 20, 1999.

STATEMENT REGARDING FEDERALLY SPONSORED RESEARCH/DEVELOPMENT

This invention was made with United States government support awarded by the following agencies: NIH HD28619. The United States has certain rights in this invention.

BACKGROUND OF THE INVENTION

This invention relates to methods useful in reducing serum bilirubin and thus the incidence and severity of infant jaundice. More particularly, it relates to the use of casein (or a salt thereof such as sodium caseinate), whey, and/or certain hydrolyzed casein formulations to supplement, while not interfering with, breast feeding.

Pediatricians recommend breast feeding as the most preferred way to feed most human neonates. However, breast feeding has been associated with increased levels of neonatal jaundice. Neonatal jaundice is mostly likely to occur during the first month (especially the first week) after a baby has been born.

Bilirubin is a red bile pigment formed during the catabolism of certain compounds such as hemoglobin. Human infants produce more bilirubin per unit of body weight than do adults because of greater red blood cell mass and shorter red blood cell life span. Bilirubin is poorly soluble in water and requires conjugation for excretion from the body.

Bilirubin is conjugated with glucuronic acid within the endoplasmic reticulum of the hepatocyte. Bilirubin conjugates in the intestine can act as a substrate for either bacterial or endogenous tissue β-glucuronidase. This enzyme hydrolyzes glucuronic acid from bilirubin glucuronide. The resulting unconjugated bilirubin produced is more rapidly absorbed from the intestine. This intestinal absorption of free bilirubin results in increased serum bilirubin levels in some neonates, which has been associated with infant jaundice.

There have been suggestions that adding aspartic acid and/or malic acid to the diet is a possible therapy for neonatal jaundice, due to inhibition of β-glucuronidase. See our laboratory's PCT publication WO 01/13743. The disclosure of this publication and of all other publications referred to herein are incorporated by reference as if fully set forth herein. While including exogenous aspartic and/or malic acid in a breast feeding baby's diet reduces the incidence of infant jaundice, it is desirable to further optimize the inhibition and treatment of such jaundice.

It is known that infants fed certain complex infant formulas having carbohydrates, fats, vitamins, sodium caseinate, and/or casein hydrolysate have lower levels of infant jaundice. See G. Gourley, et al., 103 Gastroenterology 660–667 (1992); G. Gourley, et al., 25 J. Ped. Gast. & Nutr. 267–272 (1997); and G. Gourley, 44 Advances in Pediatrics 173–229, Chapter 6 (1997). However, because many infant formulas are designed as complete substitutes for breast feeding, they can interfere with the willingness of a baby to breast feed. Thus, a mother will likely lose the benefits of breast feeding when the jaundice problem arises if a standard infant formula solution is prescribed.

While cow milk also contains casein and whey, and has been fed to some infants, any attempt to substitute cow milk for human breast milk for a neonate would have similar adverse implications for restarting breast feeding. Moreover, there are also other concerns regarding the use of cow milk by very young neonates.

Thus, it can be seen that a need exists for the development of improved infant supplements which are effective in avoiding and reducing the severity of infant jaundice, and yet do not significantly interfere with breast feeding.

SUMMARY OF THE INVENTION

The present invention provides methods of administering a dietary supplement to a human infant. One administers to the human infant on a given day human breast milk, and on that same day administers to the human infant a supplement which is essentially free of carbohydrate (and preferably also essentially free of fat) comprising an additive selected from the group consisting of casein, salts of casein, whey, and a hydrolysate of casein.

In preferred forms the infant is less than one month old (even more preferably less than two weeks old) at the time of the administration. The supplement can be provided before the infant exhibits symptoms of jaundice (as a prophylactic), or it can be provided as a therapeutic treatment to reduce bilirubin levels. The most preferred additive is a sodium caseinate/whey mixture.

In another aspect the invention provides a method of reducing serum bilirubin levels in a human infant. One administers to the human infant on a given day human breast milk, and on that same day administers to the human infant a supplement which is essentially free of carbohydrate (and preferably also essentially free of fat) comprising an additive selected from the group consisting of casein, salts of casein, whey, and a hydrolysate of casein. Using this method, the serum bilirubin level of the infant is reduced.

Another form of the invention provides a supplement dose for use on a single day with a breast feeding baby. The supplement dose is essentially free of carbohydrate and less than 50 ml (preferably 30 ml or less) in volume. The dose contains between 0.1 gm and 10 gm of a material selected from the group consisting of casein, salts of casein (such as sodium caseinate), whey, and casein hydrolysates, and a liquid carrier. The liquid carrier can be water, or an aqueous solution containing appropriate ions such as potassium and sodium, or in another suitable liquid.

Yet another form of the invention provides a supplement dose for use on a single day with a breast feeding human baby. The supplement dose is dry and essentially free of carbohydrate, and contains between 0.1 gm and 10 gm of a material selected from the group consisting of casein, salts of casein, whey, and casein hydrolysates. The supplement dose is packaged with instructions for mixing at least a portion of the dose in breast milk.

The present invention provides supplement doses of the above kind which are effective in reducing the incidence and severity of infant jaundice (yet are small enough to avoid interfering with breast feeding), supplement doses of the above kind which help reduce serum bilirubin levels, and methods for using such doses.

These and still other advantages of the present invention will be apparent from the description which follows. The following description is merely of the preferred embodiments. The claims should therefore be looked to in order to understand the full scope of the invention.

BRIEF DESCRIPTION OF THE DRAWINGS

In FIGS. 1–4 it is believed that the essentially solid line is the L-aspartic acid group, that the line with short dashes is the casein/whey mixture group, and that the line with longer dashes is the casein hydrolysate group.

DESCRIPTION OF THE PREFERRED EMBODIMENTS

Figure 1:
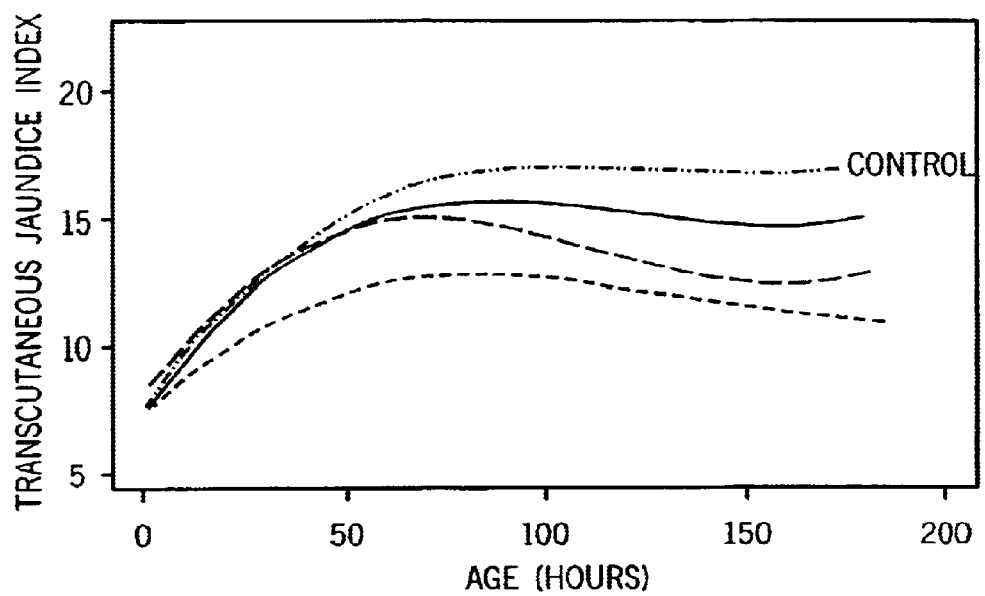
FIG. 1 is a graph showing a statistical averaging of jaundice index levels of infants subjected to four different test protocols.

Forty breast feeding human newborns were divided into four test groups. One test group received no supplement and thus just followed a normal breast feeding regime. The second test group received six daily doses of supplement, with each dose being 5 ml of water containing 0.3 gm of whey, and 0.2 gm of sodium caseinate. A third test group received six daily doses, with each dose being 5 ml of a solution created by mixing 3.6 gm of aspartic acid, 694 mg of potassium hydroxide and 226 mg of sodium hydroxide to 100 ml of distilled water (pH about 6.1).

The fourth test group received six daily doses, with each dose being 5 ml water containing 0.5 gm of the casein hydrolysate fraction of Nutramigen® infant formula. Nutramigen® is a commercially available infant formula obtainable from Mead Johnson Company. Mead Johnson kindly provided to us just the casein hydrolysate portion of that formula (without the carbohydrate, fat or vitamins). They derived the casein hydrolysate from standard casein, using well known procedures.

Under each protocol the jaundice levels of the infants were measured daily with a non-invasive transcutaneous device, the Hill-Rom Air Shields/Minolta Jaundice Meter 102 marketed by Hill-Rom Air-Shields (Hatboro, Pa.). This meter utilizes principles of skin reflectance by pressing a photoprobe against the skin with the simultaneous emission of a strobe light. This light transilluminates subcutaneous tissue and is reflected back to a spectrophotometric module.

After separation of this light into blue and green components with a dichrotic mirror the optical density of the light is measured with photocells. The difference between the optical densities of blue and green light is a measure of yellow intensity (corrected for hemoglobin). This yellow intensity is displayed numerically on the meter and is termed the "jaundice index". There is a linear relationship between the numeric readout and the yellow color imparted to skin by subcutaneous bilirubin. Typically the higher the index, the more jaundice.

Excreted bilirubin derivatives were measured by HPLC. In this regard, stool extracts were prepared as described in G. Gourley et al., 99 Gastroenterology 1705–1709 (1990) with the following modifications: After the bile pigments were extracted into the upper organic layer, this upper layer was removed and pooled with a triple extraction of the protein interface at the bottom of the upper layer. This extraction of the protein interface was accomplished by removing the interface, adding 0.1 ml dimethylformamide, sonicating for one minute, and centrifugation (12,427×g for 1 minute).

This pooling resulted in 0.5 ml which was then refrigerated (minus 20° C.×15 minutes) to precipitate any residual protein, recentrifuged (12,741×g for 5 minutes), the clarified organic extract was transferred to a 0.22 micron nylon microfuge centrifuge filter (MSI, Westboro, Mass.), recentrifuged (6,370×g for 2 minutes), and 20 µl of the extract was analyzed for bile pigments using reverse-phase high performance liquid chromatography (HPLC).

The HPLC system consisted of a Hewlett Packard (Brookfield, Wis.) diode array detector (model 1090) chemstation and pump with other details of the method as previously described in the above G. Gourley et al. article. Bilirubin and bilirubin conjugate detection was carried out at 436 nm, bandwidth 4 nm minus a reference of 554 nm, bandwidth 22 nm. Since the molar extinction coefficients for bilirubin, bilirubin diglucuronide and bilirubin monoglucuronide are nearly identical (see generally W. Spivak et al., 234 J. Biochem. 101–109 (1986)), the standard curve derived for bilirubin can be used to quantify all three bile pigments using the coumarin 6 internal standard.

Figure 2:
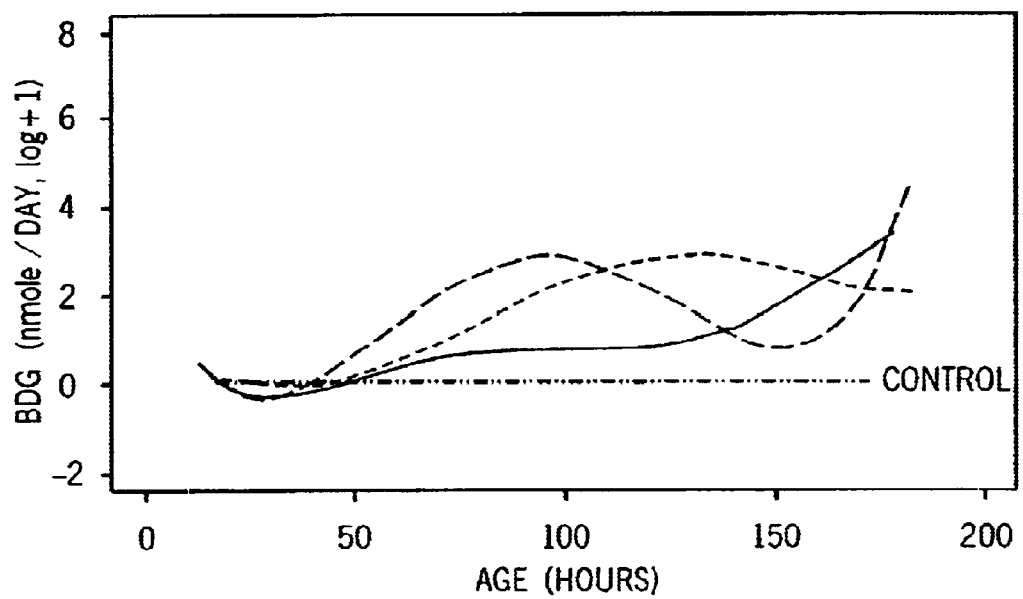
FIG. 2 is a graph presenting bilirubin diglucuronide excretion models for the four test groups.
Figure 3:
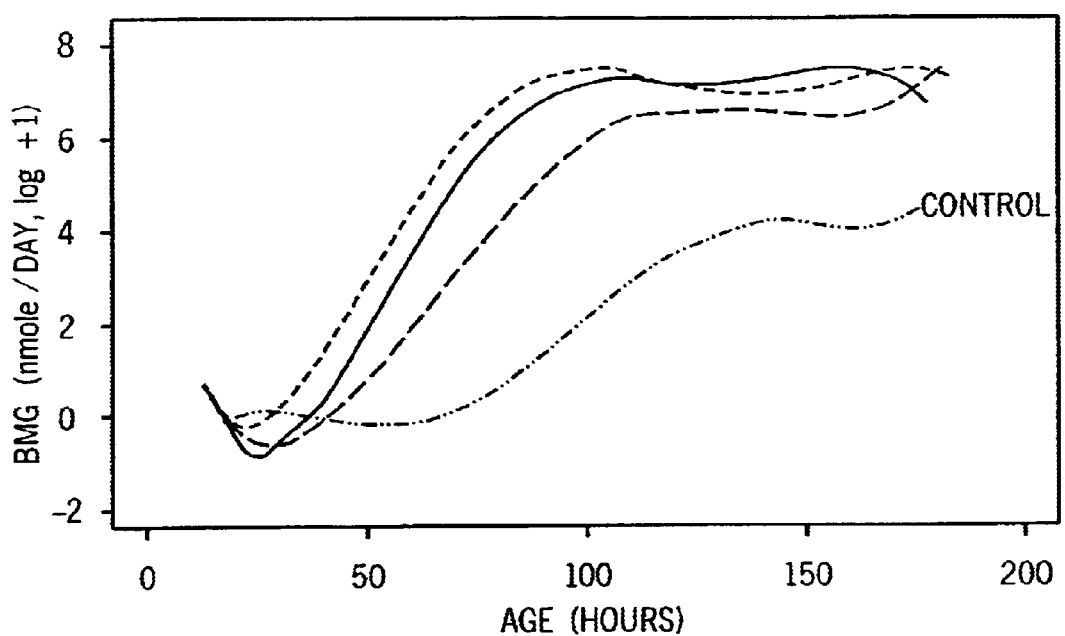
FIG. 3 is a graph presenting bilirubin monoglucuronide excretion models for the four test groups.
Figure 4:
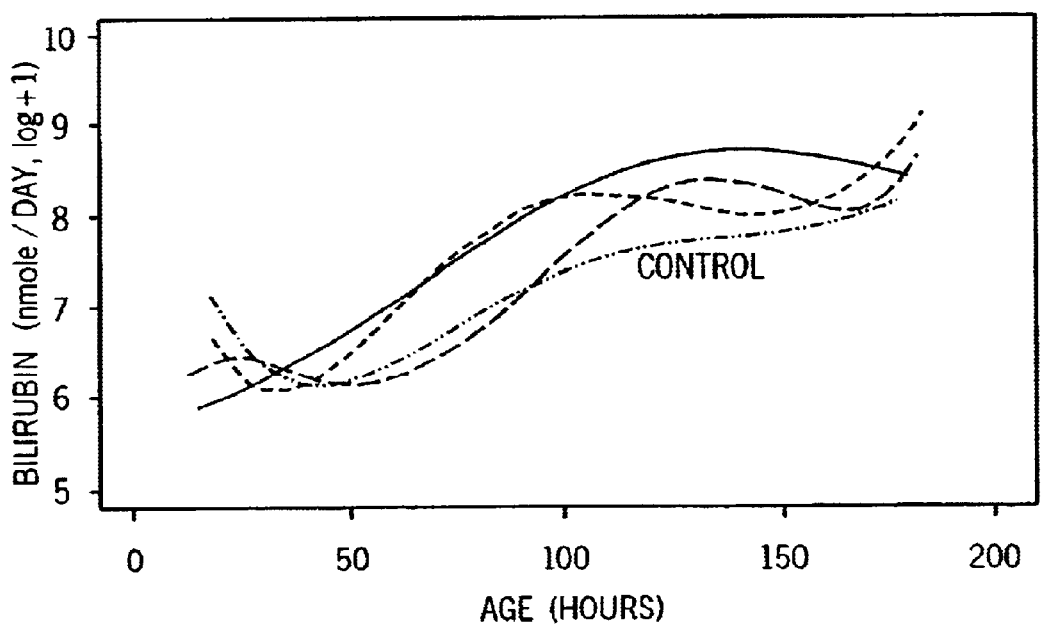
FIG. 4 is a graph presenting unconjugated bilirubin excretion models for the four test groups.

As can be seen from FIGS. 1–4, the three non-control test groups showed marked reductions in jaundice index and significant increases in bilirubin variant excretion. The caseinate/whey group is believed to have averaged the best jaundice index improvement, with the casein hydrolysate group believed to have the second best improvement. While the tests also confirmed that L-aspartic acid reduces jaundice levels in humans, these tests indicate that there are other aspects of casein hydrolysate which assist the L-aspartic acid's effect. Further, the caseinate and whey reduced the incidence of jaundice even though these components contain no significant amounts of L-aspartic acid.

Particularly surprising is that these results were achieved using extremely low levels of additive. Because of this, we are not seeing problems with continued breast feeding as a result of these additives. A total of 30 ml of liquid per day is suggested for a typical baby, with it being preferred that the 30 ml be divided into six separate doses to mimic typical breast feeding frequency. However, the entire daily dosage of supplement might be delivered at once or in 2–5 increments (albeit that may be slightly more disruptive of breast feeding, and it is conceivable that that might be less effective).

The present invention is not to be considered limited to the specific examples described above. There are other modifications that are meant to be within the scope of the invention. For example, a dry powder (without aqueous carrier) could be mixed directly into the breast milk. Thus, the claims should be looked to in order to judge the full scope of the invention.

Industrial Applicability

The present invention provides compounds useful for infant supplements, and methods of administering such compounds.

We claim:

1. A method of administering a dietary supplement to a human infant, comprising:

administering to the human infant on a day human breast milk; and on that same day administering to the human infant a supplement which is free of carbohydrate comprising an additive selected from the group consisting of casein, salts casein whey, and hydrolysates of casein.

2. The method according to claim 1, wherein the infant is less than one month old at the time of the administration.

3. The method according to claim 1, wherein the infant exhibited symptoms of jaundice prior to the administration.

4. The method according to claim 1, wherein the infant had not exhibited symptoms of jaundice prior to the administration.

5. The method according to claim 1, whereby a serum bilirubin level is reduced.

6. The method according to claim 1, wherein the additive is sodium caseinate.

7. The method according to claim 1, wherein the additive is whey.

8. The method according to claim 1, wherein the additive is a caseinate/whey mixture.

9. The method according to claim 1, wherein the additive is a hydrolysate of casein.

10. The method according to claim 1, wherein the infant is administered less than 10 gm of the additive on the day.

11. A method of reducing serum bilirubin levels in a human infant, comprising:

administering to the human infant on a day human breast milk; and on that same day administering to the human infant a supplement which is free of carbohydrate and comprises an additive selected from the group consisting of casein, salts of casein, whey, and hydrolysates of casein;

whereby the serum bilirubin level of the infant is reduced.

12. A supplement dose for use on a single day with a breast feeding baby, the supplement dose being free of carbohydrate and less than 50 ml in volume, the dose comprising:

between 0.1 gm and 10 gm of a material selected from the group consisting of casein, salts of casein, whey, and casein hydrolysates; and a liquid carrier.

13. The supplement dose of claim 12, wherein the supplement dose is no greater than 30 ml in volume.

14. A supplement dose for use on a single day with a breast feeding human baby, the supplement dose being dry and free of carbohydrate, the dose comprising between 0.1 gm and 10 gm of a material selected from the group consisting of casein, salts of casein, whey, and casein hydrolysates, wherein the supplement dose is packaged with instructions for mixing at least a portion of the dose in breast milk.

* * * * *

UNITED STATES PATENT AND TRADEMARK OFFICE
CERTIFICATE OF CORRECTION

PATENT NO.    : 6,627,213 B2
DATED         : September 30, 2003
INVENTOR(S)   : Glenn R. Gourley and Bill L. Kreamer It is certified that error appears in the above-identified patent and that said Letters Patent is hereby corrected as shown below:

<u>Column 5,</u>
Line 2, change "salts casein whey," to -- salts of casein, whey, --

Signed and Sealed this

Sixth Day of January, 2004

JAMES E. ROGAN
*Director of the United States Patent and Trademark Office*